United States Patent [19]

Kanmera et al.

[11] Patent Number: 5,252,705
[45] Date of Patent: Oct. 12, 1993

[54] PEPTIDE DERIVATIVES

[75] Inventors: Tatsuhiko Kanmera, Yokohama; Akihisa Mori; Yoshihide Nakao, both of Machida; Kenichiro Nakao, Tama, all of Japan

[73] Assignee: Mitsubishi Kasei Corporation, Tokyo, Japan

[21] Appl. No.: 778,926

[22] PCT Filed: Apr. 19, 1990

[86] PCT No.: PCT/JP90/00513
§ 371 Date: Dec. 11, 1991
§ 102(e) Date: Dec. 11, 1991

[87] PCT Pub. No.: WO91/16341
PCT Pub. Date: Oct. 31, 1991

[30] Foreign Application Priority Data
Apr. 12, 1990 [JP] Japan .................... 2-96951

[51] Int. Cl.$^5$ .................. A61K 37/02; C07K 7/10
[52] U.S. Cl. ........................................ 530/324
[58] Field of Search ............... 530/324; 514/12, 21

[56] References Cited

U.S. PATENT DOCUMENTS

| | | | |
|---|---|---|---|
| 3,886,132 | 5/1975 | Brewer et al. | 530/324 X |
| 4,105,602 | 8/1978 | Colescott et al. | 530/324 |
| 4,423,037 | 12/1983 | Rosenblatt et al. | 530/324 X |
| 5,114,843 | 5/1992 | Rosenblatt et al. | 530/324 X |
| 5,116,952 | 5/1992 | Martin et al. | 530/399 |

FOREIGN PATENT DOCUMENTS 8800596  1/1988  PCT Int'l Appl.

OTHER PUBLICATIONS

Dayhoff, Atlas of Protein Sequence and Structure, vol. 5, p. 96, 1972.

*Primary Examiner*—Michael G. Wityshyn
*Assistant Examiner*—C. Sayala
*Attorney, Agent, or Firm*—Wenderoth, Lind & Ponack

[57] ABSTRACT

The present invention relates to the peptides consisting of 25–50 amino acid residues and comprising the following peptide sequence:

Leu-Met-His-Asn-Leu-Gly-Lys-Ser-Ile-Gln-Asp-
Leu-Arg-Arg-Arg-Phe-Phe-Leu-His-His-Leu-Ile-
Ala-Glu-Ile                                      (I)

and amides and salts thereof. The peptides have stronger inhibitory activity against hPTH when compared with conventional inhibitors, and therefore, they are expected to be useful for the treatment of various diseases associated with calcium or phosphoric acid metabolism such as hypercalcemia and osteoporosis, or diseases associated with PTH and PTHrP.

1 Claim, No Drawings

PEPTIDE DERIVATIVES

FIELD OF ART

The present invention relates to novel peptide derivatives. In more particular, it relates to parathyroid hormone antagonists.

BACKGROUND OF THE INVENTION

Parathyroid hormone (referred to as PTH hereinafter) is a peptide hormone consisting of 84 amino acid residues, which is responsible for bone and calcium metabolism. A peptide fragment consisting of the first to 34th amino acid residues at the N-terminal of PTH, which is called PTH (1-34), has the same biological activity as PTH. On the other hand, other peptide fragments which lack the first few N-terminal amino acid residues, PTH (3-34), PTH (7-34), and the like, are known to suppress PTH activity.

Recently, it has been found that a PTH-related peptide (referred to as PTHrP hereinafter) derived from human carcinoma exhibits biological activity similar to PTH, and its chemical structure has been determined (Suva et al, Science, Vol.237, 893, 1987). The human PTHrP is a polypeptide consisting of 141 amino acid residues. It has biological activity similar to that of PTH, such as elevation of blood calcium level, acceleration of born absorption, lowering of blood phosphorous level, lowering of urinary calcium level, increasing of urinary cAMP level, and activation of hydroxylase at the 1-position of vitamin D in kidney (Horiuchi et al, Science, Vol.238, 1988; Kemp et al, Science, Vol.238, 1988).

Primary structure of PTHrP has poor similarity to that of PTH although partial structure of PTHrP at the amino terminal shows similarity to that of PTH. In spite of the fact, fragments of PTHrP, which lack a few amino terminal residues, such as PTHrP (3-34), suppress PTH activity likewise in PTH (Rabbani et al, oral speech at the meeting of the America Bone Metablism Association, 1988).

PTH derivatives such as [Tyr$^{34}$]-hPTH (3-34)-NH$_2$ and PTHrP derivatives such as hPTHrP (3-34)-NH$_2$ are known as a PTH antagonist. However, there has been a need to discover move potent PTH antagonist activity. The present invention relates to the peptides consisting of 25-50 amino acid residues and comprising the following peptide sequence, and amides and salts thereof.

Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile (Seq Id No. 1)        (I)

The following abbreviations are used in this text.
Asp: aspartic acid
Thr: threonine
Ser: serine
Asn: asparagine
Gln: glutamine
Glu: glutamic acid
Gly: glycine
Ala: alanine
Met: methionine
Ile: isoleucine
Leu: leucine
Phe: phenylalanine
Lys: lysine
His: histidine
Arg: arginine
Boc: t-butoxycarbonyl
Z: benzyloxycarbonyl
OcHx: cyclohexyl ester
OBzl: benzyl ester
Bzl: benzyl
Tos: p-toluenesulfonyl
Cl-Z: 2-chlorobenzyloxycarbonyl The peptide derivatives of the present invention contain at least the peptide sequence represented by the formula (I) mentioned above. For instance, the peptide derivatives of the invention may be represented by the following formula (II):

X-Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-Y-z        (II)

wherein X represents H, (Seq. ID Nos: 2–5), H-Gln (Seq. ID Nos: 6–9), H-A-Gln, (Seq. ID Nos. 6–9) H-Glu-A-Gln- (Seq. Id. Nos: 14–17), or Ser-Glu-A-Gln- (Seq. ID Nos: 18–21), wherein A is Ile, Thr, Val, or Leu; Y represents His-Thr-Ala, His-Thr-Ala-Glu-Ile-Arg-Ala, His-Thr-Ala-Glu-Ile-Arg-Ala-Thr-Ser-Glu-Val, His-Thr-Ala-Glue-Ile-Arg-Ala-Thr-Ser-Glu-Val-Ser-Pro-Asn-Ser-Lys-Pro-Asn; Z represents OH or NH$_2$.

The following Table 1 lists specific examples of the peptide derivatives of the invention.

TABLE 1

| X—Leu—Met—His—Asn—Leu—Gly—Lys—Ser—Ile—Gln—Asp—Leu—Arg—Arg—Arg—Phe—Phe—Leu—His—His—Leu—Ile—Ala—Glu—Ile—Y—Z | | | |
|---|---|---|---|
| Compound No. | X | Y | Z |
| 1 | H—Ser—Glu—Ile—Gln | His—Thr—Ala | NH$_2$ (SEQ ID NO: 18) |
| 2 | H—Glu—Ile—Gln | His—Thr—Ala | NH$_2$ (SEQ ID NO: 14) |
| 3 | H—Ile—Gln | His—Thr—Ala | NH$_2$ (SEQ ID NO: 10) |
| 4 | H—Gln | His—Thr—Ala | NH$_2$ (SEQ ID NO: 6) |
| 5 | H | His—Thr—Ala | NH$_2$ (SEQ ID NO: 2) |
| 6 | H—Ser—Glu—Ile—Gln | His—Thr—Ala | OH (SEQ ID NO: 18) |
| 7 | H—Ser—Glu—Ile—Gln | His—Thr—Ala—Glu—Ile—Arg—Ala | NH$_2$ (SEQ ID NO: 19) |
| 8 | H—Ser—Glu—Ile—Gln | His—Thr—Ala—Glu—Ile—Arg—Ala—Thr—Ser—Glu—Val | NH$_2$ (SEQ ID NO:20) |
| 9 | H—Ser—Glu—Ile—Gln | His—Thr—Ala—Glu—Ile—Arg—Ala—Thr—Ser—Glu—Val—Ser—Pro—Asn—Ser—Lys— | NH$_2$ (SEQ ID NO: 21) |

TABLE 1-continued

X—Leu—Met—His—Asn—Leu—Gly—Lys—Ser—Ile—Gln—Asp—Leu—Arg—Arg—
Arg—Phe—Phe—Leu—His—His—Leu—Ile—Ala—Glu—Ile—Y—Z

| Compound No. | X | Y | Z | |
|---|---|---|---|---|
| | | Pro—Asn | | |
| 10 | H—Ser—Glu—Val—Gln | His—Thr—Ala | NH$_2$ | (SEQ ID NO: 18) |
| 11 | H—Ser—Glu—Thr—Gln | His—Thr—Ala | NH$_2$ | (SEQ ID NO: 18) |
| 12 | H—Ser—Glu—Leu—Gln | His—Thr—Ala | NH$_2$ | (SEQ ID NO: 18) |

The peptide derivatives of the invention may be used after conversion to pharmacologically acceptable salts thereof, such as hydrochloride or acetate.

The PTHrP derivatives of the invention represented by the formula (I) or (II) may be prepared by repeating condensation reaction between relevant protected amino acids by means of conventional solid phase method, said reaction being sequentially conducted starting from C-terminal and according to the amino acid sequence shown in formula (I) or (II), and removing the protective groups and carrier to which the C-terminal amino acid residue has been linked by known methods such as acid decomposition and aminolysis. The peptide synthetic method mentioned above and the starting amino acid derivatives used therein are described in detail in various text books (See Izumiya et al, "Basis and Practice of Peptide Synthesis", published by Maruzen, 1985; Gross and Meienhofer's, "The Peptides", Vol.2, Academic Press, 1980).

The solid phase carriers used in the peptide synthesis for preparing the peptide derivatives of the present invnetion may be conventional ones, and specific examples are polystyrene resins of substituted benzyl type, polystyrene resins of hydroxymethylphenylacetic amide type, substituted benzhydrylpolystyrene resins or polyacrylamide resins having a functional group for binding to a peptide. Amino acids condensation may be also conventional, and dicyclohexylcarbodiimide (DDC), acid anhydride, and activated ester methods may be used.

Protective groups in the starting protected amino acids may be groups which are known in conventional peptide synthesis and easily removed by conventional means such as acid decomposition, reduction or aminolysis. Specific examples of amino protective group are formyl; trifluoroacetyl; benzyloxycarbonyl; substituted benzyloxycarbonyls such as (ortho- or para-) chlorobenzyloxycarbonyl, and (ortho- or para-) bromobenzyloxycarbonyl; and aliphatic oxycarbonyl such as t-butoxycarbonyl and t-amyloxycarbonyl. Carboxylic acid in amino acids may be protected by being converted to ester group. As the ester group, there may be mentioned benzyl ester; substituted benzyl ester such as methoxybenzyl ester; alkyl esters such as cyclohexyl ester, cycloheptyl ester, or t-butyl ester. Guanidino group does not require any protective group, but may be protected by nitro; or arylsulfonyl such as tosyl, methoxybenzenesulfonyl, or mesithylenesulfonyl. Protecting groups for imidazole include tosyl, benzyl, and dinitrophenyl. Hydroxy groups present in serine and threonine molecules may be non-protected or protected by benzyl or substituted benzyl. The indole group in tryptophan molecule may be non-protected or protected by formyl or the like.

The final deprotection and detachment of a resultant peptide from the carrier may be conducted by the action of anhydrous hydrogen floride in the presence of one of various scavengers. Examples of the scavengers are anisole, (ortho-, metha-, or para-) cresol, dimethylsulfide, thiocresol, ethanediol, and mercaptopyridine, which are all conventional in peptide synthesis. Purification of the resultant peptide may be conducted by means of conventional methods, such as gel-filtration, ion-exchange chromatography, and high- or low-pressure reverse phase chromatography. The peptide thus purified may be converted to its salt by the use of gel-chromatography equilibrated with aqueous acetic acid or aqueous hydrochloric acid.

BEST MODE FOR PRACTICING THE INVENTION

The following examples are presented by way of illustration of certain specific embodiments of the invention. The examples are representative only and should not be construed as limiting in any respect.

EXAMPLE 1

Synthesis of Ser-Glu-Ile-Gln-Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-His-Thr-Ala-NH$_2$ (compound 1 in Table 1)

The tile peptide was synthesized by routine solid phase method. As the solid phase carrier, 1% cross-linked 4-methylbenzylhydrylamine polystyrene (amino group content: 0.5 mmol) was used. Amino acid derivatives used for the peptide synthesis were;

Box-Ala, Boc-Asp(OcHx), Boc-Asn, Boc-Arg(Tos), Boc-Gly, Boc-Glu(OcHx), Boc-Gln, Boc-His(Tos), Boc-Ile, Boc-Leu, Boc-Lys(Cl-Z), Boc-Met, Boc-Phe, Boc-Ser(Bzl), Boc-Thr(Bzl), Boc-Val

The elongation of peptide chain was performed by repeating the steps described in Table 2.

TABLE 2

| Treatment | number of repeats | Time (min) |
|---|---|---|
| Deprotection [Treatment 1] | | |
| 1. washing with dichloromethane | 1 | 1.0 |
| 2. washing with 50% trifluoroacetic acid/dichloromethane | 1 | 5.0 |
| 3. deprotection with 50% trifluoro-acetic acid/dichloromethane | 1 | 25 |
| 4. washing with dichloromethane | 1 | 1.0 |
| Neutralization [Treatment 2] | | |
| 1. 10% diisopropylethylamine /dichloromethane | 2 | 2.0 |
| 2. washing with dichloromethane | 2 | 5.0 |
| 3. washing with dimethylformamide | 5 | 1.0 |
| Condensation* [Treatment 3] | | |
| 1. symmetric acid anhydride of tert-butoxycarbonylamino acid (2-equivalents)**/dimetylformamide | 1 | 1.0 |
| 2. washing with dimethylformamide | 5 | 1.0 |
| 3. washing with dichloromethane | 5 | 1.0 |

The carrier and protective groups were removed according to known HF method. In detail, protected peptide-polystyrene was incubated in 10% para-cresol, 65% dimetyl sulfide, and 25% anhydrous hydrogen fluoride (20 ml) at 0° C. for 2 hours, and then the reaction mixture was evaporated to remove the solvent under reduced pressure and treated with 5% paracresol and 95% anhydrous hydrogen fluoride at 0° C. for 1 hour. After evaporation of the reaction mixure under reduced pressure, the residue was washed with ethyl acetate, extracted with 1M acetic acid, and lyophilized to obtain crude peptide. The crude peptide was applied to reverse phase high pressure chromatography, and eluted with linear gradient of water-acetonitrile containing 0.1% trifluoroacetic acid. After lyophilization, the material was applied to CM Toyopearl 650S (1.5×30 cm) in 10 mM ammonium acetate (pH6.0), and separated and purified with linear gradient of 20 mM-1.0M sodium acetate. The fraction containg desired compound was gel filtrated through Sephadex G25 (15×50 cm) preequilibrated with 2% acetic acid, and then lyophilized, and converted to the acetate by gel filtration previously described to obtain the pure title compound.

Yield:31 mg

Amino acid analysis : Degraded materials obtained by hydrolysis in 5.5M hydrochloric acid at 110° C. for 48 hours were analized in an amino acid analizer. Theoretical values are shown in parenthesis. Correction on degradation of amino acids during the hydrolysis was not done.

Asp 1.93(2), Thr 0.96(1), Ser 1.56(2), Glue 4.07(4) Gly 0.94(1), Ala 2.01(2), Met 0.91(1), Ile 3.84(4) Leu 5.19(5), Phe 1.94(2), Lys 0.95(1), His 3.85(4) Arg 3.13(3)

Optical ratation $[\alpha]^{25}_D$: −66° (C=0.24, 1M acetic acid)

EXAMPLE 2

Synthesis of Ile-Gln-Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-His-Thr-Ala-NH$_2$ (compound 3 in Table 1).

The title peptide was synthesized by the method as described in Example 1.

Optical raotation $[\alpha]^{25}_D$:−65° (C=0.1, 1M acetic acid)

EXAMPLE 3

Synthesis of Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-His-Thr-Ala-NH$_z$ (compound 5 in Table 1).

The title peptide was synthesized by the method as described in Example 1.

Optical ratation $[\alpha]^{25}_D$:−62° (C=0.1, 1M acetic acid)

EXAMPLE 4

Synthesis of Ser-Glu-Ile-Gln-Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-His-Thr-Ala-Glu-Ile-Arg-Ala-NH$_2$ (compund 7 in Table 1).

The title peptide was synthesized by the method as described in Example 1.

Optical ratation $[\alpha]^{25}_D$: −95° (C=0.13, 1M acetic acid)

EXPERIMENT

Determination of PTH antagonism

Method

PTH antagonism of the peptide derivatives of the invention was determined on the basis of cAMP production using cultured osteoblast MC3T3-E1 derived from mice.

The cultured cells were plated on 12 well multiwell-culture plate at a ratio of $1 \times 10^5$ cells/well. Using α-modified MEM containing 10% quassifetal bovine serum as a culture medium, the cells were cultured at 37° C. under 95% air-5% CO$_2$ for 3 days. The medium was exchanged by α-modified MEM containing 1% bovine serum albumin and incubated for 6 hours. The medium was again exchanged by α-modified MEM containing the peptide derivative in various concentrations, $5 \times 10^{-9}$ M hPTH (1–34), 1% bovine serum albumin, and 1 mM isobutyl methylxanthine, and further incubated.

After one hour incubation, the medium and the cells were separated. The separated medium was used as a test sample for determination of cAMP without further treatment. The separated cells was treated with 90% n-propyl alcohol to extract cAMP according to Yamaguchi et al method (Journal of Biological Chemistry, Vol.262, 7711–7718, 1987). cAMP determination was conducted using a cAMP-radioimmunoassay kit which is commercially available. Table 3 shows 50% inhibition of cAMP production caused by the peptide derivatives of the invention when the amount of cAMP produced by $5 \times 10^{-9}$ M hPTH (1–34) is defined as 100%. As a control, [Tyr$^{34}$]-hPTH (3–34)-NH$_2$ and hPTHrP (3–34)-NH$_2$, which are known as a PTH antagonist, were employed.

TABLE 3

| Compound No. | IC$_{50}$ |
|---|---|
| Compound 1 | 0.007 |
| Compound 2 | 0.008 |
| Compound 3 | 0.015 |
| Compound 4 | 0.476 |
| [Tyr$^{34}$]- hpTH (3–34) - NH$_2$ | 1 |
| hpTHrp (3–34) - NH$_2$ | 0.087 |

Results

Table 3 shows that the compounds of the present invention exhibit 50% inhibition at a concentration of 1/140 as compared with that of [Tyr$^{34}$]-hPTH (3–34)-NH$_2$, and at a concentraiton of 1/12 as compared with hPTHrP (3–34)-NH$_2$.

Industrial utility

The peptide derivatives of the present invention have stronger inhibitory activity against hPTH when compared with conventional inhibitors, and therefore, they are expected to be useful for the treatment of various diseases associated with calcium or phosphoric acid metabolism such as hypercalcemia and osteoporosis, or diseases associated with PTH and PTHrP.

What is claimed is:

1. Peptides consisting of 28–32 amino acid residues and comprising the following peptide sequence:

$$\text{X-Leu-Met-His-Asn-Leu-Gly-Lys-Ser-Ile-Gln-Asp-Leu-Arg-Arg-Arg-Phe-Phe-Leu-His-His-Leu-Ile-Ala-Glu-Ile-His-Thr-Ala}  \quad (I)$$

wherein X represents H, H-Gln, H-A-Gln-, H-Glu-A-Gln, or Ser-Glu-A-Gln-, wherein A is Ile, Thr, Val, or Leu, and amides and salts thereof.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 25 amino acid residues
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

```
Leu Met His Asn Leu Gly Lys Ser Ile Gln Asp Leu Arg Arg Arg
1               5                   10                  15

Phe Phe Leu His His Leu Ile Ala Glu Ile
20                  25
```

( 2 ) INFORMATION FOR SEQ ID NO:2:

( i ) SEQUENCE CHARACTERISTICS:
        ( A ) LENGTH: 28 amino acid residues
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

(vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:
  (A) LIBRARY:
  (B) CLONE:

(viii) POSITION IN GENOME:
  (A) CHROMOSOME/SEGMENT:
  (B) MAP POSITION:
  (C) UNITS:

(ix) FEATURE:
  (A) NAME/KEY: modified-site
  (B) LOCATION: 28
  (C) IDENTIFICATION METHOD:
  (D) OTHER INFORMATION: /note="Ala-OH or Ala-NH2"

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:2:

```
Leu Met His Asn Leu Gly Lys Ser Ile Gln Asp Leu Arg Arg Arg
 1               5                  10                   15
Phe Phe Leu His His Leu Ile Ala Glu Ile His Thr Xaa
20                  25
```

(2) INFORMATION FOR SEQ ID NO:3:

(i) SEQUENCE CHARACTERISTICS:
    (A) LENGTH: 32 amino acid residues
    (B) TYPE: amino acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:

( A ) CHROMOSOME/SEGMENT:
            ( B ) MAP POSITION:
            ( C ) UNITS:

( i x ) FEATURE:
            ( A ) NAME/KEY: modified-site
            ( B ) LOCATION: 32
            ( C ) IDENTIFICATION METHOD:
            ( D ) OTHER INFORMATION: /note="Ala-OH or
                Ala-NH2"

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:3:

Leu Met His Asn Leu Gly Lys Ser Ile Gln Asp Leu Arg Arg Arg
1               5                   10                  15

Phe Phe Leu His His Leu Ile Ala Glu Ile His Thr Ala Glu Ile
20              25                  30

Arg Xaa ( 2 ) INFORMATION FOR SEQ ID NO:4:

( i ) SEQUENCE CHARACTERISTICS:
                ( A ) LENGTH: 36 amino acid residues
                ( B ) TYPE: amino acid
                ( C ) STRANDEDNESS: single
                ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY: modified-site
            ( B ) LOCATION: 36
            ( C ) IDENTIFICATION METHOD:
            ( D ) OTHER INFORMATION: /note="Val-OH or
Val-NH2"

( x ) PUBLICATION INFORMATION:
            ( A ) AUTHORS:
            ( B ) TITLE:
            ( C ) JOURNAL:

(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(x i) SEQUENCE DESCRIPTION: SEQ ID NO:4:

```
Leu Met His Asn Leu Gly Lys Ser Ile Gln Asp Leu Arg Arg Arg
1               5                   10                  15

Phe Phe Leu His His Leu Ile Ala Glu Ile His Thr Ala Glu Ile
20                  25                  30

Arg Ala Thr Ser Glu Xaa
35
```

(2) INFORMATION FOR SEQ ID NO:5:

(i) SEQUENCE CHARACTERISTICS:
        (A) LENGTH: 43 amino acid residues
        (B) TYPE: amino acid
        (C) STRANDEDNESS: single
        (D) TOPOLOGY: linear (i i) MOLECULE TYPE:

(i i i) HYPOTHETICAL:

(i v) ANTI-SENSE:

(v) FRAGMENT TYPE:

(v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY:
        (B) CLONE:

(v i i i) POSITION IN GENOME:
        (A) CHROMOSOME/SEGMENT:
        (B) MAP POSITION:
        (C) UNITS:

(i x) FEATURE:
        (A) NAME/KEY: modified-site
        (B) LOCATION: 43
        (C) IDENTIFICATION METHOD:
        (D) OTHER INFORMATION: /note="Asn-OH or
        Asn-NH2"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(x i) SEQUENCE DESCRIPTION: SEQ ID NO:5:

```
Leu Met His Asn Leu Gly Lys Ser Ile Gln Asp Leu Arg Arg Arg
1               5                   10                  15
```

Phe Phe Leu His His Leu Ile Ala Glu Ile His Thr Ala Glu Ile
20              25                  30

Arg Ala Thr Ser Glu Val Ser Pro Asn Ser Lys Pro Xaa
35              40

(2) INFORMATION FOR SEQ ID NO:6:

(i) SEQUENCE CHARACTERISTICS:
        (A) LENGTH: 29 amino acid residues
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified-site
        (B) LOCATION: 29
        (C) IDENTIFICATION METHOD:
        (D) OTHER INFORMATION: /note="Ala-OH or
            Ala-NH2"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:6:

Gln Leu Met His Asn Leu Gly Lys Ser Ile Gln Asp Leu Arg Arg
1               5                   10                  15

Arg Phe Phe Leu His His Leu Ile Ala Glu Ile His Thr Xaa
20              25

(2) INFORMATION FOR SEQ ID NO:7:

(i) SEQUENCE CHARACTERISTICS:
        (A) LENGTH: 33 amino acid residues
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified-site
    (B) LOCATION: 33
    (C) IDENTIFICATION METHOD:
    (D) OTHER INFORMATION: /note="Ala-OH or Ala-NH2"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:7:

```
Gln Leu Met His Asn Leu Gly Lys Ser Ile Gln Asp Leu Arg Arg
 1               5                  10                  15

Arg Phe Phe Leu His His Leu Ile Ala Glu Ile His Thr Ala Glu
20                  25                  30

Ile Arg Xaa
```

(2) INFORMATION FOR SEQ ID NO:8:

(i) SEQUENCE CHARACTERISTICS:
        (A) LENGTH: 37 amino acid residues
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:

```
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY: modified-site
              ( B ) LOCATION: 37
              ( C ) IDENTIFICATION METHOD:
              ( D ) OTHER INFORMATION: /note="Val-OH or
                    Val-NH2"

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO:

( x i ) SEQUENCE DESCRIPTION: SEQ ID NO:8:
```

Gln  Leu  Met  His  Asn  Leu  Gly  Lys  Ser  Ile  Gln  Asp  Leu  Arg  Arg
1              5                        10                       15

Arg  Phe  Phe  Leu  His  His  Leu  Ile  Ala  Glu  Ile  His  Thr  Ala  Glu
20                  25                       30

Ile  Arg  Ala  Thr  Ser  Glu  Xaa
35

```
( 2 ) INFORMATION FOR SEQ ID NO:9:

( i ) SEQUENCE CHARACTERISTICS:
              ( A ) LENGTH: 44 amino acid residues
              ( B ) TYPE: amino acid
              ( C ) STRANDEDNESS: single
              ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
              ( A ) ORGANISM:
              ( B ) STRAIN:
              ( C ) INDIVIDUAL ISOLATE:
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY: modified-site
              ( B ) LOCATION: 44
```

(C) IDENTIFICATION METHOD:
(D) OTHER INFORMATION: /note="Asn-OH or Asn-NH2"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:9:

```
Gln Leu Met His Asn Leu Gly Lys Ser Ile Gln Asp Leu Arg Arg
 1               5                  10                  15

Arg Phe Phe Leu His His Leu Ile Ala Glu Ile His Thr Ala Glu
20                  25                  30

Ile Arg Ala Thr Ser Glu Val Ser Pro Asn Ser Lys Pro Xaa
35                  40
```

(2) INFORMATION FOR SEQ ID NO:10:

(i) SEQUENCE CHARACTERISTICS:
(A) LENGTH: 30 amino acid residues
(B) TYPE: amino acid
(C) STRANDEDNESS: single
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: modified-site
(B) LOCATION: 1
(C) IDENTIFICATION METHOD:
(D) OTHER INFORMATION: /note="Ile, Thr, Val or Leu"

(ix) FEATURE:
(A) NAME/KEY: modified-site
(B) LOCATION: 30
(C) IDENTIFICATION METHOD:
(D) OTHER INFORMATION: /note="Ala-OH or Ala-NH2"

(x) PUBLICATION INFORMATION:
(A) AUTHORS:
(B) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:10:

```
Xaa Gln Leu Met His Asn Leu Gly Lys Ser Ile Gln Asp Leu Arg
 1               5                  10                  15

Arg Arg Phe Phe Leu His His Leu Ile Ala Glu Ile His Thr Xaa
20                  25                  30
```

(2) INFORMATION FOR SEQ ID NO:11:

(i) SEQUENCE CHARACTERISTICS:
      (A) LENGTH: 34 amino acid residues
      (B) TYPE: amino acid
      (C) STRANDEDNESS: single
      (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
      (A) ORGANISM:
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (A) LIBRARY:
      (B) CLONE:

(viii) POSITION IN GENOME:
      (A) CHROMOSOME/SEGMENT:
      (B) MAP POSITION:
      (C) UNITS:

(ix) FEATURE:
      (A) NAME/KEY: modified-site
      (B) LOCATION: 1
      (C) IDENTIFICATION METHOD:
      (D) OTHER INFORMATION: /note="Ile, Thr, Val or Leu"

(ix) FEATURE:
      (A) NAME/KEY: modified-site
      (B) LOCATION: 34
      (C) IDENTIFICATION METHOD:
      (D) OTHER INFORMATION: /note="Ala-OH or Ala-NH2"

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

( x i ) SEQUENCE DESCRIPTION: SEQ ID NO:11:

Xaa Gln Leu Met His Asn Leu Gly Lys Ser Ile Gln Asp Leu Arg
1               5                   10                  15

Arg Arg Phe Phe Leu His His Leu Ile Ala Glu Ile His Thr Ala
20                  25                  30

Glu Ile Arg Xaa ( 2 ) INFORMATION FOR SEQ ID NO:12:

( i ) SEQUENCE CHARACTERISTICS:
        ( A ) LENGTH: 38 amino acid residues
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: modified-site
        ( B ) LOCATION: 1
        ( C ) IDENTIFICATION METHOD:
        ( D ) OTHER INFORMATION: /note="Ile, Thr, Val or
            Leu"

( i x ) FEATURE:
        ( A ) NAME/KEY: modified-site
        ( B ) LOCATION: 38
        ( C ) IDENTIFICATION METHOD:
        ( D ) OTHER INFORMATION: /note="Val-OH or
            Val-NH2"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:12:

Xaa Gln Leu Met His Asn Leu Gly Lys Ser Ile Gln Asp Leu Arg
1               5                   10                  15

Arg Arg Phe Phe Leu His His Leu Ile Ala Glu Ile His Thr Ala
20                  25                  30

Glu Ile Arg Ala Thr Ser Glu Xaa
35

( 2 ) INFORMATION FOR SEQ ID NO:13:

( i ) SEQUENCE CHARACTERISTICS:
    ( A ) LENGTH: 45 amino acid residues
    ( B ) TYPE: amino acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY: modified-site
    ( B ) LOCATION: 1
    ( C ) IDENTIFICATION METHOD:
    ( D ) OTHER INFORMATION: /note="Ile, Thr, Val or
      Leu"

( i x ) FEATURE:
    ( A ) NAME/KEY: modified-site
    ( B ) LOCATION: 45
    ( C ) IDENTIFICATION METHOD:
    ( D ) OTHER INFORMATION: /note="Asn-OH or
      Asn-NH2"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:13:

Xaa Gln Leu Met His Asn Leu Gly Lys Ser Ile Gln Asp Leu Arg
1               5                   10                  15

Arg Arg Phe Phe Leu His His Leu Ile Ala Glu Ile His Thr Ala
20              25                  30

Glu Ile Arg Ala Thr Ser Glu Val Ser Pro Asn Ser Lys Pro Xaa
35              40                  45

( 2 ) INFORMATION FOR SEQ ID NO:14:

( i ) SEQUENCE CHARACTERISTICS:

(A) LENGTH: 31 amino acid residues
(B) TYPE: amino acid
(C) STRANDEDNESS: single
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: modified-site
(B) LOCATION: 2
(C) IDENTIFICATION METHOD:
(D) OTHER INFORMATION: /note="Ile, Thr, Val or Leu"

(ix) FEATURE:
(A) NAME/KEY: modified-site
(B) LOCATION: 31
(C) IDENTIFICATION METHOD:
(D) OTHER INFORMATION: /note="Ala-OH or Ala-NH2"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:14:

Glu Xaa Gln Leu Met His Asn Leu Gly Lys Ser Ile Gln Asp Leu
1               5                   10                  15

Arg Arg Arg Phe Phe Leu His His Leu Ile Ala Glu Ile His Thr
20              25                  30

Xaa (2) INFORMATION FOR SEQ ID NO:15:

(i) SEQUENCE CHARACTERISTICS:
(A) LENGTH: 35 amino acid residues
(B) TYPE: amino acid
(C) STRANDEDNESS: single
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: modified-site
                (B) LOCATION: 2
                (C) IDENTIFICATION METHOD:
                (D) OTHER INFORMATION: /note="Ile, Thr, Val or
                        Leu"

(ix) FEATURE:
                (A) NAME/KEY: modified-site
                (B) LOCATION: 35
                (C) IDENTIFICATION METHOD:
                (D) OTHER INFORMATION: /note="Ala-OH or
                        Ala-NH2"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:15:

Glu Xaa Gln Leu Met His Asn Leu Gly Lys Ser Ile Gln Asp Leu
1               5                   10                  15

Arg Arg Arg Phe Phe Leu His His Leu Ile Ala Glu Ile His Thr
20              25                  30

Ala Glu Ile Arg Xaa
35

(2) INFORMATION FOR SEQ ID NO:16:

(i) SEQUENCE CHARACTERISTICS:
                (A) LENGTH: 39 amino acid residues
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:

(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: modified-site
(B) LOCATION: 2
(C) IDENTIFICATION METHOD:
(D) OTHER INFORMATION: /note="Ile, Thr, Val or Leu"

(ix) FEATURE:
(A) NAME/KEY: modified-site
(B) LOCATION: 39
(C) IDENTIFICATION METHOD:
(D) OTHER INFORMATION: /note="Val-OH or Val-NH2"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:16:

```
Glu Xaa Gln Leu Met His Asn Leu Gly Lys Ser Ile Gln Asp Leu
1               5                   10                  15

Arg Arg Arg Phe Phe Leu His His Leu Ile Ala Glu Ile His Thr
20              25                  30

Ala Glu Ile Arg Ala Thr Ser Glu Xaa
35
```

(2) INFORMATION FOR SEQ ID NO:17:

(i) SEQUENCE CHARACTERISTICS:
(A) LENGTH: 46 amino acid residues
(B) TYPE: amino acid
(C) STRANDEDNESS: single
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:

( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: modified-site
                    ( B ) LOCATION: 2
                    ( C ) IDENTIFICATION METHOD:
                    ( D ) OTHER INFORMATION: /note="Ile, Thr, Val or
                            Leu"

( i x ) FEATURE:
                    ( A ) NAME/KEY: modified-site
                    ( B ) LOCATION: 46
                    ( C ) IDENTIFICATION METHOD:
                    ( D ) OTHER INFORMATION: /note="Asn-OH or
                            Asn-NH2"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:17:

Glu  Xaa  Gln  Leu  Met  His  Asn  Leu  Gly  Lys  Ser  Ile  Gln  Asp  Leu
1                   5                        10                         15

Arg  Arg  Arg  Phe  Phe  Leu  His  His  Leu  Ile  Ala  Glu  Ile  His  Thr
20                       25                       30

Ala  Glu  Ile  Arg  Ala  Thr  Ser  Glu  Val  Ser  Pro  Asn  Ser  Lys  Pro
35                       40                       45

Xaa ( 2 ) INFORMATION FOR SEQ ID NO:18:

( i ) SEQUENCE CHARACTERISTICS:
                    ( A ) LENGTH: 32 amino acid residues
                    ( B ) TYPE: amino acid
                    ( C ) STRANDEDNESS: single
                    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified-site
    (B) LOCATION: 3
    (C) IDENTIFICATION METHOD:
    (D) OTHER INFORMATION: /note="Ile, Thr, Val or Leu"

(ix) FEATURE:
    (A) NAME/KEY: modified-site
    (B) LOCATION: 32
    (C) IDENTIFICATION METHOD:
    (D) OTHER INFORMATION: /note="Ala-OH or Ala-NH2"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:18:

```
Ser Glu Xaa Gln Leu Met His Asn Leu Gly Lys Ser Ile Gln Asp
 1           5                   10                  15

Leu Arg Arg Arg Phe Phe Leu His His Leu Ile Ala Glu Ile His
20                  25                  30

Thr Xaa
```

(2) INFORMATION FOR SEQ ID NO:19:

(i) SEQUENCE CHARACTERISTICS:
        (A) LENGTH: 36 amino acid residues
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified-site (B) LOCATION: 3
                    (C) IDENTIFICATION METHOD:
                    (D) OTHER INFORMATION: /note="Ile, Thr, Val or
                        Leu"

(ix) FEATURE:
                    (A) NAME/KEY: modified-site
                    (B) LOCATION: 36
                    (C) IDENTIFICATION METHOD:
                    (D) OTHER INFORMATION: /note="Ala-OH or
                        Ala-NH2"

(x) PUBLICATION INFORMATION:
                    (A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:19:

```
Ser Glu Xaa Gln Leu Met His Asn Leu Gly Lys Ser Ile Gln Asp
1               5                   10                  15
Leu Arg Arg Arg Phe Phe Leu His His Leu Ile Ala Glu Ile His
20                  25                  30
Thr Ala Glu Ile Arg Xaa
35
```

(2) INFORMATION FOR SEQ ID NO:20:

(i) SEQUENCE CHARACTERISTICS:
                    (A) LENGTH: 40 amino acid residues
                    (B) TYPE: amino acid
                    (C) STRANDEDNESS: single
                    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY: modified-site
                    (B) LOCATION: 3
                    (C) IDENTIFICATION METHOD:
                    (D) OTHER INFORMATION: /note="Ile, Thr, Val or
                        Leu"

(ix) FEATURE:
                    (A) NAME/KEY: modified-site ( B ) LOCATION: 40
( C ) IDENTIFICATION METHOD:
( D ) OTHER INFORMATION: /note="Val-OH or
    Val-NH2"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:20:

```
Ser Glu Xaa Gln Leu Met His Asn Leu Gly Lys Ser Ile Gln Asp
 1           5                  10                       15

Leu Arg Arg Arg Phe Phe Leu His His Leu Ile Ala Glu Ile His
20                  25                  30

Thr Ala Glu Ile Arg Ala Thr Ser Glu Xaa
35                  40
```

( 2 ) INFORMATION FOR SEQ ID NO:21:

( i ) SEQUENCE CHARACTERISTICS:
    ( A ) LENGTH: 47 amino acid residues
    ( B ) TYPE: amino acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY: modified-site
    ( B ) LOCATION: 3
    ( C ) IDENTIFICATION METHOD:
    ( D ) OTHER INFORMATION: /note="Ile, Thr, Val or
        Leu"

( i x ) FEATURE:
    ( A ) NAME/KEY: modified-site
    ( B ) LOCATION: 47
    ( C ) IDENTIFICATION METHOD:
    ( D ) OTHER INFORMATION: /note="Asn-OH or
        Asn-NH2"

( x ) PUBLICATION INFORMATION:
    ( A ) AUTHORS:

(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:21:

Ser Glu Xaa Gln Leu Met His Asn Leu Gly Lys Ser Ile Gln Asp
1               5                   10                  15

Leu Arg Arg Arg Phe Phe Leu His His Leu Ile Ala Glu Ile His
20                  25                  30

Thr Ala Glu Ile Arg Ala Thr Ser Glu Val Ser Pro Asn Ser Lys
35                  40                  45

Pro Xaa